United States Patent
Li, Sr. et al.

(10) Patent No.: US 11,447,456 B1
(45) Date of Patent: Sep. 20, 2022

(54) CRYSTALLINE FORM OF LAMOTRIGINE HYDRATE, METHOD FOR PREPARING THE SAME AND COMPOSITION COMPRISING THE SAME

(71) Applicant: Shanghai Aucta Pharmaceuticals Co., Ltd., Shanghai (CN)

(72) Inventors: Shoufeng Li, Sr., Shanghai (CN); Yong Wang, Shanghai (CN)

(73) Assignee: SHANGHAI AUCTA PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 17/366,295

(22) Filed: Jul. 2, 2021

(30) Foreign Application Priority Data

Apr. 16, 2021 (CN) .......................... 202110412683.1

(51) Int. Cl.
| | | |
|---|---|---|
| *C07D 253/075* | (2006.01) | |
| *A61K 9/08* | (2006.01) | |
| *A61K 47/32* | (2006.01) | |
| *A61K 47/38* | (2006.01) | |
| *A61K 9/10* | (2006.01) | |
| *C07B 63/04* | (2006.01) | |

(52) U.S. Cl.
CPC ............ *C07D 253/075* (2013.01); *A61K 9/08* (2013.01); *A61K 9/10* (2013.01); *A61K 47/32* (2013.01); *A61K 47/38* (2013.01); *C07B 63/04* (2013.01); *C07B 2200/13* (2013.01)

(58) Field of Classification Search
CPC ................................................ C07D 253/075
USPC ....................................................... 544/182
See application file for complete search history.

(56) References Cited

U.S. PATENT DOCUMENTS

| | | | | |
|---|---|---|---|---|
| 6,861,426 | B2 * | 3/2005 | Garti | ........................ A61P 25/08 |
| | | | | 514/242 |
| 7,390,807 | B2 * | 6/2008 | Garti | .................. C07D 253/075 |
| | | | | 514/242 |
| 2009/0312544 | A1 | 12/2009 | Van Deynse et al. | |

FOREIGN PATENT DOCUMENTS

| | | |
|---|---|---|
| CN | 101506178 A | 8/2009 |
| CN | 101795673 A | 8/2010 |
| CN | 104940930 A | 9/2015 |
| CN | 106491539 A | 3/2017 |
| CN | 110545818 A | 12/2019 |
| CN | 113214177 A | 8/2021 |
| WO | 2005003104 A2 | 1/2005 |
| WO | 2008068619 A2 | 6/2008 |

OTHER PUBLICATIONS

Allen, L.V., "Lamotrigine 1 mg/mL Oral Suspension", U.S. Pharmacist, May 15, 2015, vol. 40, No. 5, ISSN: 0148-4818, pp. 64-65.
Rani, et al: "Full Factorial Design in Formulation of Lamotrigine Suspension Using Locust Bean Gum", Int. J. Sci., Dec. 31, 2013, vol. 11, No. 2, ISSN: 0972-768X, pp. 751-760.

* cited by examiner

*Primary Examiner* — Nizal S Chandrakumar
(74) *Attorney, Agent, or Firm* — Fox Rothschild LLP

(57) ABSTRACT

The invention relates to a crystalline form of lamotrigine hydrate, a method for preparing the same and a composition comprising the same, and in particular, to a lamotrigine hydrate form A, a method for preparing the lamotrigine hydrate form A and a composition comprising the lamotrigine hydrate form A.

19 Claims, 3 Drawing Sheets

CRYSTALLINE FORM OF LAMOTRIGINE HYDRATE, METHOD FOR PREPARING THE SAME AND COMPOSITION COMPRISING THE SAME

TECHNICAL FIELD

This disclosure relates to a crystalline form of a lamotrigine hydrate, a method for preparing the same and a composition comprising the same, and in particular, to a lamotrigine hydrate form A, a method for preparing the lamotrigine hydrate form A and a composition comprising the lamotrigine hydrate form A.

BACKGROUND

Epilepsy is one of the most common neurological disorders. An epileptic attack may lead to progressive loss in brain function, causing cognitive impairment and mental decline. A sudden epileptic attack tends to cause accidental injuries, while a sustained epileptic attack may endanger life and seriously affect the quality of life of a patient, which generally leads to lifelong medication.

Lamotrigine (under the trade name Lamictal) plays an anti-epileptic role mainly by blocking voltage-gated sodium channels, reducing the influx of sodium, and increasing the stability of neurons. Lamotrigine was marketed in Europe and the United States in 1991 and 1994, respectively. Currently, lamotrigine is used in monotherapy or adjunctive therapy of various types of epilepsy, especially in infant, adolescent and elderly patients, with an efficacy comparable to that of phenytoin and carbamazepine.

At present, 4 dosage forms of lamotrigine have been approved to go into the market in China and abroad: a common tablet, a chewable tablet, an orally disintegrating tablet and a slow-release tablet. As there is no marketable oral liquid formulation of lamotrigine, it is often required to crush a lamotrigine tablet into powder to prepare a liquid formulation in use, in order to facilitate oral administration to children or patients with dysphagia. However, this extemporaneous formulation may easily result in inaccurate dosing as well as drug contamination Lamotrigine is a BCS (biopharmaceutical classification system) class II drug molecule, which has a poor solubility in aqueous media, although decreasing pH may increase solubility to some extent, with only a limited effect. The Chinese Patent Applications CN201510288845.X and CN201510350210.8 disclose medical prescriptions of a lamotrigine oral liquid formulation and a method for preparing thereof, where the drug concentration of the formulation is less than 2 mg/ml, which cannot meet clinical requirements. In case that a high concentration of medical prescription is required, it is necessary to add an organic solvent, which is not favorable for oral administration to children.

It is also not desirable to develop a suspension with an anhydrous lamotrigine. The applicant has found by experiments that although no bulk crystal was found on a newly prepared lamotrigine suspension that was made through a common method, after standing at room temperature for 3 days, a large number of bulk crystals appeared and tended to become larger over time, resulting in inaccurate dosing for patients. The Chinese Patent Application CN201611175342.2A discloses a method for inhibiting a hydrate, but such inhibiting effect can only be maintained for 24 hours, causing inconvenience in long-term medication of patients.

Various properties of a pharmaceutical active ingredient, such as the melting point, solubility, stability and bioavailability, may be affected by a crystalline state thereof. Since eutectics or hydrates of a drug may effectively improve the crystallization and physical and chemical properties of the drug through a hydrogen bond or other non-covalent bonds, without compromising the active ingredients of the drug, they have become focuses in the development of pharmaceutical solid formulations.

So far, a variety of lamotrigine eutectics have been reported. Lamotrigine salts that have been reported include 1:1 lamotrigine-4-hydroxybenzoic acid, 1:1 lamotrigine-saccharin, 1:3 lamotrigine-acetic acid, 1:1 lamotrigine-propionic acid, 2:1 lamotrigine-adipic acid, 2:1 lamotrigine-malic acid, 1:1 lamotrigine-methyl p-hydroxybenzoate, 1:1 lamotrigine-nicotine, 1:1:1 lamotrigine-nicotine monohydrate, 1:1 lamotrigine-acetamide. Lamotrigine solvates that have been reported include 1:2 lamotrigine methanol solvate, 1:1:1 lamotrigine ethanol monohydrate. However, as no liquid dosage form of the above eutectics has been developed, the problem of inaccurate dosing of lamotrigine is still yet to solve.

There are problems with current lamotrigine formulations, such as inaccurate dosing, low loading of the solution form, and poor physical stability of the suspension.

SUMMARY OF THE INVENTION

In a first aspect, the invention provides a lamotrigine hydrate form A, where an XRPD spectrum of the lamotrigine hydrate form A includes characteristic peaks at diffraction angles (2θ) of about 11.5±0.2°, 13.4±0.2°, 15.0±0.2°, 16.5±0.2°, 19.2±0.2°, 26.9±0.2° and 27.7±0.2°, and no characteristic peak at one or more of diffraction angles (2θ) of 15.9±0.2°, 20.5±0.2°, 23.5±0.2°, 28.2±0.2° and 30.7±0.2°.

In some embodiments, the XRPD spectrum of the lamotrigine hydrate form A includes characteristic peaks at substantially same diffraction angles (2θ) as shown in FIG. 1. In other words, the peaks in the XRPD spectrum are located at substantially same positions as those shown in FIG. 1.

In some embodiments, the lamotrigine hydrate form A has a purity of at least about 80%.

In a second aspect, the invention provides a method for preparing a suspension of a lamotrigine hydrate form A, comprising the steps of: adding lamotrigine particles and a thickener to an aqueous phase; dispersing uniformly; and standing at a low temperature to obtain a suspension comprising the lamotrigine hydrate form A, where the lamotrigine particles have a particle size (D90) from about 1 to 30 μm.

In a third aspect, the invention provides a method for preparing a lamotrigine hydrate form A, comprising filtering the suspension of lamotrigine hydrate form A of the invention, to obtain the lamotrigine hydrate form A.

In some embodiments, the lamotrigine particles have a particle size (D90) of about 8 to 12 μm.

In some embodiments, the thickener is selected from hydrocolloids, such as xanthan gum, guar gum, locust bean gum and carrageenan; cellulose derivatives, such as sodium carboxymethyl cellulose, hydroxypropyl cellulose, methyl cellulose and hydroxypropyl methyl cellulose; polysaccharides, such as starch and pregelatinized starch; alginates, such as sodium alginate; acrylic acid copolymers, such as carbomer; and aluminum magnesium silicate, and combinations thereof. In some embodiments, the thickener is about 1-7 parts by weight, on the basis that the lamotrigine particles are about 10 parts by weight.

In some embodiments, the aqueous phase is purified water or comprises purified water and one or more of the following: an essence, a pH modifier and a sweetener. In some embodiments, the aqueous phase is about 100 to 5000 parts by weight, on the basis that the lamotrigine particles are about 10 parts by weight.

In some embodiments, the dispersing uniformly is implemented by mechanical stirring, magnetic stirring, and/or manual shaking for about 1-120 minutes.

In some embodiments, the low temperature is lower than about 25° C. The standing at a low temperature is carried out for at least about 30 minutes.

In some embodiments, the dispersing uniformly is separated by a time interval of up to about 12 hours from the standing at a low temperature.

In some embodiments, the suspension may be applied as a suspension.

In some embodiments, more than about 80% of lamotrigine is present in the form of the lamotrigine hydrate form A.

In a fourth aspect, the invention provides a composition comprising the lamotrigine hydrate form A of the invention and one or more pharmaceutically acceptable excipients.

In some embodiments, the composition further comprises one or more other medicaments selected from oxcarbazepine, carbamazepine, topiramate, and lacosamide.

In some embodiments, the composition is in a dosage form selected from a tablet, a capsule, a powder, and a suspension.

In some embodiments, more than about 80% of lamotrigine in the composition is present as the lamotrigine hydrate form A.

In some embodiments, the pharmaceutically acceptable excipients are selected from one or more of a thickener, a filler, a sweetener, a pH modifier and a preservative.

In some embodiments, the composition of the invention comprises:
 about 10 parts by weight of the lamotrigine hydrate form A;
 about 1-5 parts by weight of xanthan gum;
 about 20-60 parts by weight of mannitol;
 about 1-3 parts by weight of sucralose;
 about 2-5 parts by weight of sodium dihydrogen phosphate; and
 about 1-3 parts by weight of a combination of sodium methyl hydroxybenzoate and sodium propyl hydroxybenzoate, where the weight ratio of sodium methyl hydroxybenzoate and sodium propyl hydroxybenzoate is about 9:1.

In a fifth aspect, the invention provides a suspension comprising a lamotrigine hydrate form A, the lamotrigine hydrate form A, a solid form comprising the lamotrigine hydrate form A or a composition comprising the lamotrigine hydrate form A, prepared by the method of the invention.

In some embodiments, in the suspension comprising lamotrigine hydrate form A, the lamotrigine hydrate form A, the solid form comprising the lamotrigine hydrate form A or the composition comprising the lamotrigine hydrate form A, more than about 80% of lamotrigine is present in the form of the lamotrigine hydrate form A.

In a sixth aspect, the invention provides a method for treating a neurological disorder, comprising administering a therapeutically effective amount of the lamotrigine hydrate form A of the invention or the composition of the invention to a subject in need thereof.

In a seventh aspect, the invention provides a use of the lamotrigine hydrate form A of the invention or the composition of the invention in preparation of a medicament for treating a neurological disorder.

In an eighth aspect, the invention provides the lamotrigine hydrate form A of the invention or the composition of the invention for use in treating a neurological disorder.

In some embodiments, the neurological disorder is selected from one or more of Alzheimer's disease, depression, multiple sclerosis, Parkinson's disease, and epilepsy.

In some embodiments, the medicament is used to treat the neurological disorder in combination with other medicaments.

In some embodiments, the medicament is in the form of a suspension.

In some embodiments, more than about 80% of lamotrigine in the medicament is present in the form of the lamotrigine hydrate form A.

DETAILED DESCRIPTION OF EMBODIMENTS

Figure 1:
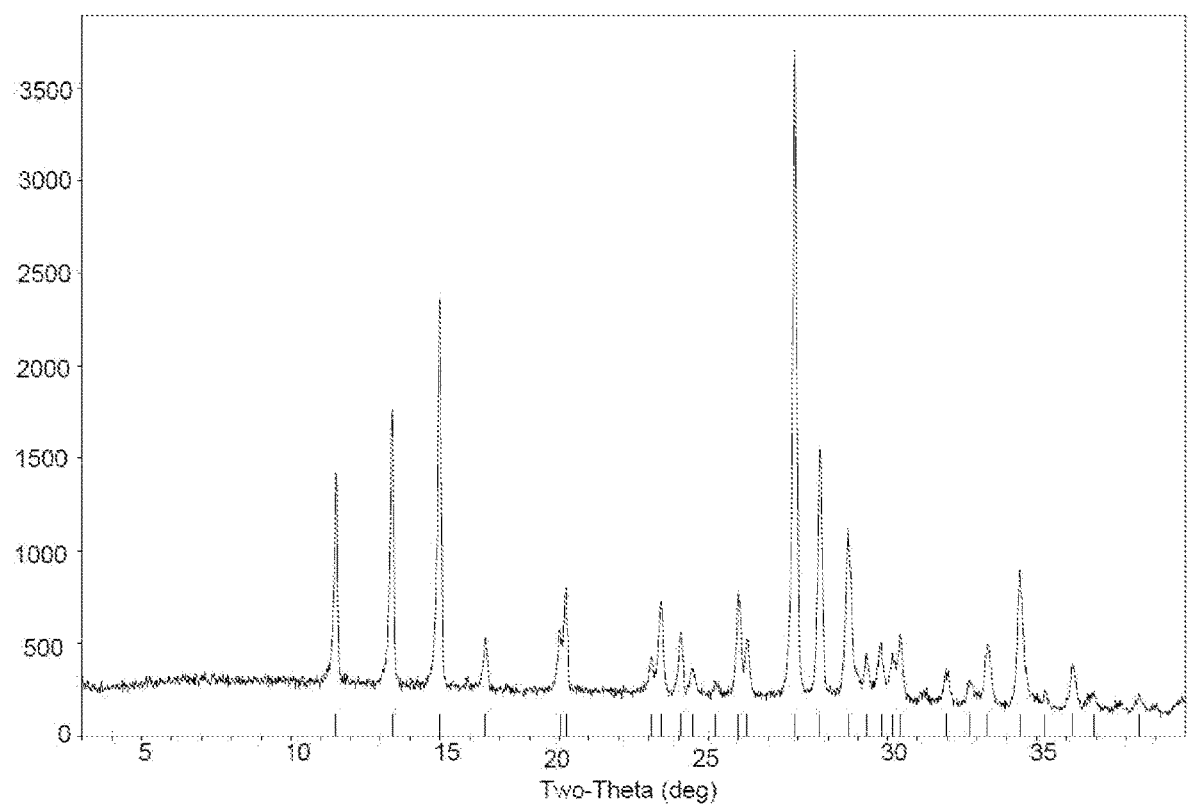
FIG. 1 shows an XRPD spectogram of a lamotrigine hydrate form A.

Unless defined otherwise, all technical and scientific terms used herein have the same meanings as those commonly understood by one of ordinary skill in the art to which this invention belongs. If there is a contradiction, the definition provided in this application shall prevail.

As used herein, the terms "comprise", "include", "have", "contain" or "relate to" and other variants thereof herein, are inclusive or open-ended and do not exclude other elements or method steps that are not listed.

As used herein, the word "about" indicates a range within an acceptable standard error of the given value as appreciated by one of ordinary skill in the art, such as ±0.05, ±0.1, ±0.2, ±0.3, ±0.5, ±1, ±2 or ±3.

As used herein, the term "amorphous" refers to any solid matter that is unordered in three dimensions. In some cases, an amorphous solid may be characterized by known techniques, including XRPD crystal diffraction analysis, solid-state nuclear magnetic resonance (ssNMR) spectroscopy, differential scanning calorimetry (DSC) or a combination thereof. An XRPD spectrum of an amorphous solid shows no obvious diffraction characteristic peak.

As used herein, the term "crystalline form" or "crystal" refers to any solid matter that exhibits a three-dimensional order, and that generates a characteristic XRPD spectrum with well peaks, as opposed to the amorphous solid matter.

As used herein, the term "XRPD spectrum (x-ray powder diffraction spectrum)" refers to a diffraction pattern observed by experiments, or parameters, data, or values derived therefrom. The XRPD spectrum is typically characterized by a peak position (abscissa) and/or peak intensity (ordinate).

As used herein, the term "2θ" refers to a peak position in degrees (°) set in an x-ray diffraction experiment, and typically refers to a unit of abscissa in the diffraction spectrum. If a reflected beam is diffracted when an incident beam forms an angle θ with a lattice surface, the experiment needs to be set to record the reflected beam as an angle 2θ.

It should be understood that a specific 2θ value of a specific crystal form mentioned herein is intended to represent a 2θ value (expressed in degrees) measured by using the x-ray diffraction experimental conditions described herein. For example, as described herein, Cu-kα (Kα1 (Å):1.540598 and Kα2 (Å):1.544426) are used as radiation sources.

As used herein, the term "substantially the same" means that changes in representative peak positions and/or intensity are taken into consideration. For example, with respect to x-ray diffraction peaks, a skilled person in the art may understand that some variations in the peak position (2θ) may be shown, usually up to 0.1-0.2 degrees, and the instrument for measuring the diffraction may also bring some variations. In addition, a skilled person in the art may understand that changes in relative peak strength may occur due to variations of instruments and factors such as crystallinity, preferred orientation, surface of the prepared sample, and other factors known to those skilled in the art, and therefore the relative peak strength should only be regarded as a qualitative measurement.

As used herein, the term "low temperature" refers to a temperature lower than the normal temperature (about 25° C.).

Crystal Form

In one aspect, the invention provides a lamotrigine hydrate form A, where an XRPD spectrum of the lamotrigine hydrate form A includes characteristic peaks at diffraction angles (2θ) of about 11.5±0.2°, 13.4±0.2°, 15.0±0.2°, 16.5±0.2°, 19.2±0.2°, 26.9±0.2° and 27.7±0.2°, and has no characteristic peak at one or more of diffraction angles (2θ) of 15.9±0.2°, 20.5±0.2°, 23.5±0.2°, 28.2±0.2° and 30.7±0.2°.

In some embodiments, the XRPD spectrum of the lamotrigine hydrate form A has no characteristic peak at a diffraction angle (2θ) of about 15.9±0.2°. In some embodiments, the XRPD spectrum of the lamotrigine hydrate form A has no characteristic peak at a diffraction angle (2θ) of about 30.7±0.2°. In some embodiments, the XRPD spectrum of the lamotrigine hydrate form A has no characteristic peak at diffraction angles (2θ) of about 23.5±0.2°, 28.2±0.2° and 30.7±0.2°. In a preferred embodiment, the XRPD spectrum of the lamotrigine hydrate form A has no characteristic peak at diffraction angles (2θ) of about 15.9±0.2°, 20.5±0.2°, 23.5±0.2°, 28.2±0.2° and 30.7±0.2°.

In some embodiments, the XRPD spectrum of the lamotrigine hydrate form A includes characteristic peaks at the substantially the same diffraction angles (2θ) as shown in FIG. 1. In other words, the positions of the peaks in the XRPD spectrum are substantially the same as those present in FIG. 1.

Purity of the lamotrigine hydrate form A herein is determined by XRPD quantitative analysis. The XRPD quantitative analysis is based on the principle that intensity of diffracted rays of each phase increases with the relative content of the phase in a mixture. A constant reference material is added to a tested powder sample to prepare a composite sample. The content of the phase to be tested is determined by measuring the ratio of the intensity of a diffracted ray of the phase to be tested to the intensity of a diffracted ray of an internal standard in the composite sample. $Al_2O_3$ is selected as the reference material.

In some embodiments, purity of the lamotrigine hydrate form A is at least about 60%. In some embodiments, purity of the lamotrigine hydrate form A is at least about 70%. In some embodiments, purity of the lamotrigine hydrate form A is at least about 80%. Preferably, purity of the lamotrigine hydrate form A is at least about 90%. More preferably, purity of the lamotrigine hydrate form A is at least about 95%. Most preferably, the lamotrigine hydrate form A is substantially pure. The "substantially pure" herein means that the form contains impurities of less than about 3% by weight, including other crystalline forms, solvated forms or amorphous forms.

Figure 2:
FIG. 2 shows a microscopic photograph of a lamotrigine hydrate form A.

The XRPD spectrum of the lamotrigine hydrate form A with a purity of at least about 95% is shown in FIG. 1. The XRPD spectrum of the lamotrigine hydrate form A with a purity of at least about 95% described above has a series of characteristic peaks at diffraction angles (2θ) of about 11.5±0.2°, 13.4±0.2°, 15.0±0.2°, 16.5±0.2°, 19.2±0.2°, 26.9±0.2° and 27.7±0.2°, and has no characteristic peak at diffraction angles (2θ) of about 15.9±0.2°, 20.5±0.2°, 23.5±0.2°, 28.2±0.2° and 30.7±0.2°. The lamotrigine hydrate form A with a purity of at least about 95% described above shows an appearance of short prism under a microscope, as shown in FIG. 2. It is shown in a thermogravimetric analysis on the lamotrigine hydrate form A with a purity of at least about 95% described above that with a weight loss of about 6.6% at 190° C., the lamotrigine hydrate form A is a monohydrate.

Preparation Method

In another aspect, the invention provides a method for preparing a suspension of comprising lamotrigine hydrate form A, comprising the steps of: adding lamotrigine particles and a thickener to an aqueous phase; dispersing uniformly; and standing at a low temperature, to obtain the suspension comprising lamotrigine hydrate form A, where the lamotrigine particles have a particle size (D90) of about 1 to 30 μm.

In another aspect, the invention provides a method for preparing lamotrigine hydrate form A, comprising filtering the suspension of the invention, to obtain the lamotrigine hydrate form A. In some embodiments, the method may further comprise washing the crystals with water during the filtering to remove the thickener (or suspending agent) adhered to the crystals.

In the present application, stability of the lamotrigine hydrate form A, i.e., stability of the crystal form and stability of the particle size, in the aqueous phase, is of great importance to the development of lamotrigine liquid formulations. The stability of the crystal form means that the crystal form maintains consistent in the aqueous phase over a period of time. As dissolution rate varies between crystal forms, resulting in significant differences in stability therefrom, the stability of crystal properties can be maintained by avoiding introduction of other crystal forms, thereby ensuring safety and reliability of a product. Particle size stability means that the particle size of the crystal in the aqueous phase is maintained within a certain range over a period of time. Excessive particle size may affect the uniform state of a drug and eventually lead to inaccurate dosing. Experiences reveals that particle size of the crystal exceeding 85 μm may easily result in a nonuniform system. In the present application, effects of different preparation conditions on the stability of the crystal form and particle size are investigated.

In some embodiments, the suspension comprising lamotrigine hydrate form A or the lamotrigine hydrate form A is prepared by using lamotrigine particles having a particle size (D90) of about 1, 2, 4, 6, 8, 10, 12, 14, 15, 16, 18, 20, 25 or 30 μm. In some embodiments, the suspension comprising lamotrigine hydrate form A or the lamotrigine hydrate form A is prepared by using lamotrigine particles having a particle size (D90) of about 1 μm. In some embodiments, the suspension comprising lamotrigine hydrate form A or the lamotrigine hydrate form A is prepared by using lamotrigine particles having a particle size (D90) of about 15 µm. In some embodiments, the suspension comprising lamotrigine hydrate form A or the lamotrigine hydrate form A is prepared by using lamotrigine particles having a particle size (D90) of about 30 µm. In a preferred embodiment, the lamotrigine particles have a particle size (D90) of about 8-12 µm. D90 means that particles having a particle size less than the particle size account for 90%.

In some embodiments, the thickener (or suspending agent) is selected from: hydrocolloids, such as xanthan gum, guar gum, locust bean gum and carrageenan; cellulose derivatives, such as sodium carboxymethyl cellulose, hydroxypropyl cellulose, methyl cellulose and hydroxypropyl methyl cellulose; polysaccharides, such as starch and pregelatinized starch; alginates, such as sodium alginate; acrylic acid copolymers, such as carbomer; and aluminum magnesium silicate; and a combination thereof.

In a preferred embodiment, the thickener is selected from xanthan gum, povidone, colloidal microcrystalline cellulose, sodium alginate, and a combination thereof. More preferably, the thickener is xanthan gum.

In some embodiments, the thickener is about 1 to 7 parts by weight, preferably about 1 to 5 parts by weight, on the basis that lamotrigine particles are about 10 parts by weight.

In some embodiments, the weight ratio of the lamotrigine particles to the thickener is from about 1:1 to about 20:1, from about 1:1 to about 15:1, from about 1:1 to about 10:1, from about 2:1 to about 10:1, from about 5:1 to about 10:1 or from about 3:1 to about 10:1. In some embodiments, the weight ratio of the lamotrigine particles to the thickener is about 10:1, about 10:2, about 10:3, about 10:4, about 10:5, about 10:6, about 10:7, or about 10:8.

In some embodiments, the suspension comprising lamotrigine hydrate form A, or the lamotrigine hydrate form A, is prepared by using about 2 parts by weight of xanthan gum, on the basis that the lamotrigine particles are about 10 parts by weight. In some embodiments, the suspension comprising lamotrigine hydrate form A, or the lamotrigine hydrate form A, is prepared by using about 3 parts by weight of xanthan gum, on the basis that the lamotrigine particles are about 10 parts by weight. In some embodiments, the suspension comprising lamotrigine hydrate form A, or the lamotrigine hydrate form A, is prepared by using about 4 parts by weight of xanthan gum, on the basis that the lamotrigine particles are about 10 parts by weight. In some embodiments, the suspension comprising lamotrigine hydrate form A, or the lamotrigine hydrate form A, is prepared by using about 6 parts by weight of xanthan gum, on the basis that the lamotrigine particles are about 10 parts by weight. In some embodiments, the suspension comprising lamotrigine hydrate form A, or the lamotrigine hydrate form A, is prepared by using about 7 parts by weight of xanthan gum, on the basis that the lamotrigine particles are about 10 parts by weight.

In some embodiments, the suspension comprising lamotrigine hydrate form A, or the lamotrigine hydrate form A, is prepared by using about 1-7 parts by weight of xanthan gum, preferably about 1-5 parts by weight of xanthan gum, on the basis that the lamotrigine particles are about 10 parts by weight.

In some embodiments, the aqueous phase is purified water. In some embodiments, the aqueous phase may further comprise another solute such as an essence, a pH modifier, or a sweetener. In some embodiments, the aqueous phase comprises purified water and one or more of an essence, a pH modifier and a sweetener.

In some embodiments, the aqueous phase is about 100-5000 parts by weight, preferably about 500-2000 parts by weight, on the basis that the lamotrigine particles are about 10 parts by weight.

In some embodiments, the suspension comprising lamotrigine hydrate form A, or the lamotrigine hydrate form A, is prepared by using about 100, 200 or 300 parts by weight of purified water, on the basis that the lamotrigine particles are about 10 parts by weight. In some embodiments, the suspension comprising lamotrigine hydrate form A, or the lamotrigine hydrate form A, is prepared by using about 500, 600 or 800 parts by weight of purified water, on the basis that the lamotrigine particles are about 10 parts by weight. In some embodiments, the suspension comprising lamotrigine hydrate form A, or the lamotrigine hydrate form A, is prepared by using about 1000 or 2000 parts by weight of purified water, on the basis that the lamotrigine particles are about 10 parts by weight. In some embodiments, the suspension comprising lamotrigine hydrate form A, or the lamotrigine hydrate form A, is prepared by using about 2500 or 4000 parts by weight of purified water, on the basis that the lamotrigine particles are about 10 parts by weight. In some embodiments, the suspension comprising lamotrigine hydrate form A, or the lamotrigine hydrate form A, is prepared by using about 5000, 6000, 7000 or 8000 parts by weight of purified water, on the basis that the lamotrigine particles are about 10 parts by weight.

In some embodiments, the suspension comprising lamotrigine hydrate form A, or the lamotrigine hydrate form A, is prepared by using about 100-5000 parts by weight of purified water, preferably 500-2000 parts by weight of purified water, on the basis that the lamotrigine particles are about 10 parts by weight.

In some embodiments, the dispersing uniformly may be implemented by one or more combinations of mechanical stirring, magnetic stirring, or manual shaking. The dispersing uniformly refers to the formation of a uniform system.

In some embodiments, the dispersing uniformly is achieved in about 1-120 minutes, preferably about 3-15 minutes. In some embodiments, the dispersing uniformly is achieved in about 1 minute, to obtain the suspension comprising lamotrigine hydrate form A, or the lamotrigine hydrate form A. In some embodiments, the dispersing uniformly is achieved in about 2 minutes, to obtain the suspension comprising lamotrigine hydrate form A, or the lamotrigine hydrate form A. In some embodiments, the dispersing uniformly is achieved in about 5 minutes, to obtain the suspension comprising lamotrigine hydrate form A, or the lamotrigine hydrate form A. In some embodiments, the dispersing uniformly is achieved in about 10 minutes, to obtain the suspension comprising lamotrigine hydrate form A, or the lamotrigine hydrate form A. In some embodiments, the dispersing uniformly is achieved in about 15 minutes, to obtain the suspension comprising lamotrigine hydrate form A, or the lamotrigine hydrate form A. In some embodiments, the dispersing uniformly is achieved in about 20 minutes, to obtain the suspension comprising lamotrigine hydrate form A, or the lamotrigine hydrate form A. In some embodiments, the dispersing uniformly is achieved in about 25 minutes, to obtain the suspension comprising lamotrigine hydrate form A, or the lamotrigine hydrate form A. In some embodiments, the dispersing uniformly is achieved in about 30 minutes, to obtain the suspension comprising lamotrigine hydrate form A, or the lamotrigine hydrate form A. In some embodiments, the dispersing uniformly is achieved in about 60 minutes, to obtain the suspension comprising lamotrigine hydrate form A, or the lamotrigine hydrate form A. In some embodiments, the dispersing uniformly is achieved in about 120 minutes. to obtain the suspension comprising lamotrigine hydrate form A, or the lamotrigine hydrate form A.

In some embodiments, the dispersing uniformly may be implemented by mechanical stirring, magnetic stirring and/or manual shaking for about 1 to 120 minutes, preferably about 3-15 minutes.

In some embodiments, in order to save the preparation time, a specific dispersion time is not set, as long as uniform dispersion is achieved.

In some embodiments, the low temperature is selected from: no more than about −20° C., no more than about −10° C., no more than about −5° C., no more than about 0° C., not more than about 4° C., not more than about 10° C., not more than about 20° C. and not more than about 25° C. In some embodiments, the low temperature is selected from about −20° C. to about 25° C., from about −20° C. to about 20° C., from about −20° C. to about 0° C., from about 0° C. to about 20° C., from about 0° C. to about 4° C. and from about 4° C. to about 20° C.

In some embodiments, the low temperature is lower than about 25° C., preferably lower than about 20° C.

In some embodiments, the suspension comprising lamotrigine hydrate form A, or the lamotrigine hydrate form A, is prepared at a low temperature of about −20° C. In some embodiments, the suspension comprising lamotrigine hydrate form A, or the lamotrigine hydrate form A, is prepared at a low temperature of about −15° C. In some embodiments, the suspension comprising lamotrigine hydrate form A, or the lamotrigine hydrate form A, is prepared at a low temperature of about −10° C. In some embodiments, the suspension comprising lamotrigine hydrate form A, or the lamotrigine hydrate form A, is prepared at a low temperature of about −5° C. In some embodiments, the suspension comprising lamotrigine hydrate form A, or the lamotrigine hydrate form A, is prepared at a low temperature of about 0° C. In some embodiments, the suspension comprising lamotrigine hydrate form A, or the lamotrigine hydrate form A, is prepared at a low temperature of about 4° C. In some embodiments, the suspension comprising lamotrigine hydrate form A, or the lamotrigine hydrate form A, is prepared at a low temperature of about 5° C. In some embodiments, the suspension comprising lamotrigine hydrate form A, or the lamotrigine hydrate form A, is prepared at a low temperature of about 10° C. In some embodiments, the suspension comprising lamotrigine hydrate form A, or the lamotrigine hydrate form A, is prepared at a low temperature of about 15° C. In some embodiments, the suspension comprising lamotrigine hydrate form A, or the lamotrigine hydrate form A, is prepared at a low temperature of about 20° C.

In some embodiments, the standing at a low temperature is implemented for at least about 30 minutes, preferably at least about 2 hours.

In some embodiments, the standing at a low temperature is implemented for about 30 minutes, to prepare the suspension comprising lamotrigine hydrate form A, or the lamotrigine hydrate form A. In some embodiments, the standing at a low temperature is implemented for about 1 hour. to prepare the suspension comprising lamotrigine hydrate form A, or the lamotrigine hydrate form A. In some embodiments, the standing at a low temperature is implemented for about 2 hours, to prepare the suspension comprising lamotrigine hydrate form A, or the lamotrigine hydrate form A. In some embodiments, the standing at a low temperature is implemented for about 8 hours, to prepare the suspension comprising lamotrigine hydrate form A, or the lamotrigine hydrate form A. In some embodiments, the standing at a low temperature is implemented for about 24 hours, to prepare the suspension comprising lamotrigine hydrate form A, or the lamotrigine hydrate form A.

In some embodiments, the standing at a low temperature is implemented in a time interval after the dispersing uniformly.

In some embodiments, the time interval between the dispersing uniformly and the standing at a low temperature is at most about 12 hours, preferably at most about 1 minute, more preferably 0.

In some embodiments, the suspension comprising lamotrigine hydrate form A, or the lamotrigine hydrate form A, is prepared with a time interval of no more than about 12 hours between the dispersing uniformly and the standing at a low temperature. In some embodiments, the suspension comprising lamotrigine hydrate form A, or the lamotrigine hydrate form A, is prepared with the time interval of no more than about 8 hours. In some embodiments, the suspension comprising lamotrigine hydrate form A, or the lamotrigine hydrate form A, is prepared with the time interval of no more than about 2 hours. In some embodiments, the suspension comprising lamotrigine hydrate form A, or the lamotrigine hydrate form A, is prepared with the time interval of no more than about 60 minutes. In some embodiments, the suspension comprising lamotrigine hydrate form A, or the lamotrigine hydrate form A, is prepared with the time interval of no more than about 30 minutes. In some embodiments, the suspension comprising lamotrigine hydrate form A, or the lamotrigine hydrate form A, is prepared with the time interval of no more than about 20 minutes. In some embodiments, the suspension comprising lamotrigine hydrate form A, or the lamotrigine hydrate form A, is prepared with the time interval of no more than about 10 minutes. In some embodiments, the suspension comprising lamotrigine hydrate form A, or the lamotrigine hydrate form A, is prepared with the time interval of no more than about 1 minute. In some embodiments, the suspension comprising lamotrigine hydrate form A, or the lamotrigine hydrate form A, is prepared with the time interval of 0.

In some embodiments, in order to save the preparation time, subsequent steps are performed directly after completion of the previous step without setting a time interval.

In some embodiments, the method for preparing a suspension comprising lamotrigine hydrate form A comprises the steps of: adding about 10 parts by weight of lamotrigine particles having a particle size (D90) of about 1-30 μm and about 1-7 parts by weight of thickeners to about 100-5000 parts by weight of the aqueous phase; dispersing uniformly; and standing at a low temperature of 25° C. for at least 30 minutes, to obtain the suspension comprising lamotrigine hydrate form A. In some embodiments, the method for preparing a suspension comprising lamotrigine hydrate form A comprises the steps of: adding about 10 parts by weight of lamotrigine particles having a particle size (D90) of about 8-12 μm and about 1-5 parts by weight of xanthan gum into about 500-2000 parts by weight of purified water; dispersing uniformly; and standing at a low temperature of 20° C. for at least 2 hours, to obtain the suspension comprising lamotrigine hydrate form A.

In some embodiments, the suspension can be used as a suspension. The suspension prepared by the method of the invention may be directly used as a suspension.

In some embodiments, further included is preparing lamotrigine particles and a thickener together with one or more of a filler, a sweetener, a pH modifier and a preservative into a dry suspension, which is then added to the aqueous phase.

In a preferred embodiment, the dry suspension is prepared by direct mixing.

In some embodiments, the filler is one or more combinations of mannitol, microcrystalline cellulose, sucrose, lactose, and is about 20-60 parts by weight, on the basis that the lamotrigine particles is about 10 parts by weight. The sweetener is one or more combinations of sucralose, aspartame, and sodium saccharin, and is about 1-3 parts by weight, on the basis that the lamotrigine particles are about 10 parts by weight. The pH modifier is one or more combinations of sodium dihydrogen phosphate, citric acid, and sodium citrate, and is about 2-5 parts by weight, on the basis that the lamotrigine particles are about 10 parts by weight. The preservative is one or more combinations of sodium propyl hydroxybenzoate, sodium methyl hydroxybenzoate, sodium benzoate and potassium sorbate, and is about 1-3 parts by weight, on the basis that the lamotrigine particles are about 10 parts by weight.

In some embodiments, more than about 60% of lamotrigine is present in the form of lamotrigine hydrate form A. In some embodiments, more than about 70% of lamotrigine is present in the form of lamotrigine hydrate form A. In some embodiments, more than about 80% of lamotrigine is present in the form of lamotrigine hydrate form A. Preferably more than about 90% of lamotrigine is present in the form of lamotrigine hydrate form A. More preferably more than about 95% of lamotrigine is present in the form of lamotrigine hydrate form A. Most preferably, more than about 97% of lamotrigine is present in the form of lamotrigine hydrate form A.

In another aspect, the invention provides a method for reconstituting a composition comprising lamotrigine particles and a thickener to form a suspension comprising lamotrigine hydrate form A immediately before use. In this method, same processes, required components and amounts as those in the method for preparing a suspension comprising lamotrigine hydrate form A described above may be used. This method may include the following steps: adding the composition comprising lamotrigine particles and a thickener to the aqueous phase; dispersing uniformly; and standing at low temperature, to obtain the suspension comprising lamotrigine hydrate form A, where the lamotrigine particles have a particle size (D90) of about 1-30 μm.

In some embodiments, the composition comprising lamotrigine particles and a thickener is reconstituted by using lamotrigine particles having a particle size (D90) of about 1 μm, to obtain the suspension comprising lamotrigine hydrate form A. In some embodiments, the composition comprising lamotrigine particles and a thickener is reconstituted by using the lamotrigine particles having a particle size (D90) of about 8 μm, to obtain the suspension comprising lamotrigine hydrate form A. In some embodiments, the composition comprising lamotrigine particles and a thickener is reconstituted by using the lamotrigine particles having a particle size (D90) of about 12 μm, to obtain the suspension comprising lamotrigine hydrate form A. In some embodiments, the composition comprising lamotrigine particles and a thickener is reconstituted by using the lamotrigine particles having a particle size (D90) of about 30 μm, to obtain the suspension comprising lamotrigine hydrate form A.

In a preferred embodiment, the lamotrigine particles have a particle size (D90) of about 8-12 μm.

In some embodiments, the thickener (suspending agent) in the composition comprising lamotrigine particles and a thickener is selected from: hydrocolloids, such as xanthan gum, guar gum, locust bean gum and carrageenan; cellulose derivatives, such as sodium carboxymethyl cellulose, hydroxypropyl cellulose, methyl cellulose and hydroxypropyl methyl cellulose; polysaccharides, such as starch and pregelatinized starch; alginates, such as sodium alginate; acrylic acid copolymers, such as carbomer; and aluminum magnesium silicate; and a combination thereof.

In a preferred embodiment, the thickener is selected from xanthan gum, povidone, colloidal microcrystalline cellulose, sodium alginate, and a combination thereof. More preferably, the thickener is xanthan gum.

In some embodiments, the thickener is about 1 to 7 parts by weight, preferably about 1 to 5 parts by weight, based on about 10 parts by weight of lamotrigine particles.

In some embodiments, in the composition comprising lamotrigine particles and a thickener, the suspension comprising lamotrigine hydrate form A is obtained by reconstituting the above composition comprising about 2 parts by weight of xanthan gum, on the basis that the lamotrigine particles are about 10 parts by weight of. In some embodiments, the suspension comprising lamotrigine hydrate form A is obtained by reconstituting the above composition comprising about 3 parts by weight of xanthan gum, on the basis that the lamotrigine particles are about 10 parts by weight. In some embodiments, the suspension comprising lamotrigine hydrate form A is obtained by reconstituting the above composition comprising about 4 parts by weight of xanthan gum, on the basis that the lamotrigine particles are about 10 parts by weight. In some embodiments, the suspension comprising lamotrigine hydrate form A is obtained by reconstituting the above composition comprising about 6 parts by weight of xanthan gum, on the basis that the lamotrigine particles are about 10 parts by weight. In some embodiments, the suspension comprising lamotrigine hydrate form A is obtained by reconstituting the above composition comprising about 7 parts by weight of xanthan gum, on the basis that the lamotrigine particles are about 10 parts by weight.

In a preferred embodiment, in the composition comprising lamotrigine particles and a thickener, the suspension comprising lamotrigine hydrate form A is obtained by reconstituting, the above composition comprising about 1-5 parts by weight of xanthan gum, on the basis that the lamotrigine particles are about 10 parts by weight.

In some embodiments, the composition comprising lamotrigine particles and a thickener may further comprise one or more of a filler, a sweetener, a pH modifier and a preservative.

In some embodiments, the aqueous phase is purified water. In some embodiments, the aqueous phase may further comprise another solute such as an essence, a pH modifier, or a sweetener. In some embodiments, the aqueous phase comprises purified water and one or more of an essence, a pH modifier and a sweetener.

In some embodiments, the aqueous phase is about 100-5000 parts by weight, preferably about 500-2000 parts by weight, on the basis that the lamotrigine particles are about 10 parts by weight.

In some embodiments, the suspension comprising lamotrigine hydrate form A is obtained by reconstitution of using about 100 parts by weight of purified water, on the basis that the lamotrigine particles are about 10 parts by weight. In some embodiments, the suspension comprising lamotrigine hydrate form A is obtained by reconstitution of using about 500 parts by weight of purified water, on the basis that the lamotrigine particles are about 10 parts by weight. In some embodiments, the suspension comprising lamotrigine hydrate form A is obtained by reconstitution of using about 1000 parts by weight of purified water, on the basis that the lamotrigine particles are about 10 parts by weight. In some embodiments, the suspension comprising lamotrigine hydrate form A is obtained by reconstitution of using about 2500 parts by weight of purified water, on the basis that the lamotrigine particles are about 10 parts by weight. In some embodiments, the suspension comprising lamotrigine hydrate form A is obtained by reconstitution of using about 5000 parts by weight of purified water, on the basis that the lamotrigine particles are about 10 parts by weight.

In some embodiments, a stable suspension comprising lamotrigine hydrate form A is obtained by reconstitution of using about 100-5000 parts by weight of purified water, preferably about 500-2000 parts by weight of purified water, on the basis that the lamotrigine particles are about 10 parts by weight.

In some embodiments, the dispersing uniformly may be implemented by one or more combinations of mechanical stirring, magnetic stirring, or manual shaking.

In some embodiments, the dispersing uniformly is implemented for about 1-120 minutes, preferably about 3-15 minutes. In some embodiments, the dispersing uniformly is implemented for about 1 minute, to obtain the suspension comprising lamotrigine hydrate form A by reconstitution. In some embodiments, the dispersing uniformly is implemented for about 2 minutes, to obtain the suspension comprising lamotrigine hydrate form A by reconstitution. In some embodiments, the dispersing uniformly is implemented for about 5 minutes, to obtain the suspension comprising lamotrigine hydrate form A by reconstitution. In some embodiments, the dispersing uniformly is implemented for about 10 minutes, to obtain the suspension comprising lamotrigine hydrate form A by reconstitution. In some embodiments, the dispersing uniformly is implemented for about 15 minutes, to obtain the suspension comprising lamotrigine hydrate form A by reconstitution. In some embodiments, the dispersing uniformly is implemented for about 20 minutes, to obtain the suspension comprising lamotrigine hydrate form A by reconstitution. In some embodiments, the dispersing uniformly is implemented for about 25 minutes, to obtain the suspension comprising lamotrigine hydrate form A by reconstitution. In some embodiments, the dispersing uniformly is implemented for about 30 minutes, to obtain the suspension comprising lamotrigine hydrate form A by reconstitution. In some embodiments, the dispersing uniformly is implemented for about 60 minutes, to obtain the suspension comprising lamotrigine hydrate form A by reconstitution. In some embodiments, the dispersing uniformly is implemented for about 120 minutes, to obtain the suspension comprising lamotrigine hydrate form A by reconstitution.

In some embodiments, the dispersing uniformly may be achieved by mechanical stirring, magnetic stirring and/or manual shaking for about 1-120 minutes, preferably about 3-15 minutes.

In some embodiments, in order to save the preparation time, no specific dispersing time is set, provided that the dispersing uniformly is achieved.

In some embodiments, the low temperature is lower than about 25° C., preferably lower than about 20° C.

In some embodiments, the suspension comprising lamotrigine hydrate form A is obtained by reconstitution at a low temperature of about −20° C. In some embodiments, the suspension comprising lamotrigine hydrate form A is obtained by reconstitution at a low temperature of about −15° C. In some embodiments, the suspension comprising lamotrigine hydrate form A is obtained by reconstitution at a low temperature of about −10° C. In some embodiments, the suspension comprising lamotrigine hydrate form A is obtained by reconstitution at a low temperature of about −5° C. In some embodiments, the suspension comprising lamotrigine hydrate form A is obtained by reconstitution at a low temperature of about 0° C. In some embodiments, the suspension comprising lamotrigine hydrate form A is obtained by reconstitution at a low temperature of about 4° C. In some embodiments, the suspension comprising lamotrigine hydrate form A is obtained by reconstitution at a low temperature of about 5° C. In some embodiments, the suspension comprising lamotrigine hydrate form A is obtained by reconstitution at a low temperature of about 10° C. In some embodiments, the suspension comprising lamotrigine hydrate form A is obtained by reconstitution at a low temperature of about 15° C. In some embodiments, the suspension comprising lamotrigine hydrate form A is obtained by reconstitution at a low temperature of about 20° C.

In some embodiments, the standing at low temperature is implemented for at least about 30 minutes, preferably at least about 2 hours.

In some embodiments, the standing at a low temperature in implemented for at least 24 hours, to obtain the suspension comprising lamotrigine hydrate form A by reconstitution. In some embodiments, the standing at a low temperature in implemented for at least 8 hours, to obtain the suspension comprising lamotrigine hydrate form A by reconstitution. In some embodiments, the standing at a low temperature in implemented for at least 2 hours, to obtain the suspension comprising lamotrigine hydrate form A by reconstitution. In some embodiments, the standing at a low temperature in implemented for at least 1 hour, to obtain the suspension comprising lamotrigine hydrate form A by reconstitution. In some embodiments, the standing at a low temperature in implemented for at least 30 minutes, to obtain the suspension comprising lamotrigine hydrate form A by reconstitution.

In some embodiments, the standing at a low temperature may be implemented in a time interval after the dispersing uniformly.

In some embodiments, the time interval between the dispersing uniformly and the standing at a low temperature is at most about 12 hours, preferably at most about 1 minute, more preferably 0.

In some embodiments, the suspension comprising lamotrigine hydrate form A is obtained by reconstitution with a time interval of no more than about 12 hours between the dispersing uniformly and the standing at a low temperature. In some embodiments, the suspension comprising lamotrigine hydrate form A is obtained by reconstitution with a time interval of no more than about 8 hours. In some embodiments, the suspension comprising lamotrigine hydrate form A is obtained by reconstitution with a time interval of no more than about 2 hours. In some embodiments, the suspension comprising lamotrigine hydrate form A is obtained by reconstitution with a time interval of no more than about 30 minutes. In some embodiments, the suspension comprising lamotrigine hydrate form A is obtained by reconstitution with a time interval of no more than about 20 minutes. In some embodiments, a suspension comprising lamotrigine hydrate form A is obtained by reconstitution with a time interval of no more than about 10 minutes. In some embodiments, the suspension comprising lamotrigine hydrate form A is obtained by reconstitution with a time interval of no more than about 1 minute. In some embodiments, the suspension comprising lamotrigine hydrate form A is obtained by reconstitution with a time interval of 0.

In some embodiments, in order to save the preparation time, subsequent steps are performed directly after completion of the previous step without setting the time interval.

Compositions and Products

In another aspect, the invention provides a composition comprising the lamotrigine hydrate form A of the invention and one or more pharmaceutically acceptable excipients.

In some embodiments, the composition may further comprise at least one additional medicament. In some embodiments, the composition further comprises one or more additional medicaments selected from oxcarbazepine, carbamazepine, topiramate and lacosamide.

In some embodiments, the lamotrigine hydrate form A or a composition thereof may also be packaged in a kit together with other medicaments. The lamotrigine hydrate form A or a composition thereof may be administered in combination with other medicaments to a patient simultaneously or successively.

In some embodiments, the composition may administer the lamotrigine hydrate form A described herein to a patient in any suitable dosage form. The dosage form includes, but is not limited to: (a) a dosage form for oral administration, including a capsule, a tablet, a granule, a sprays a syrup and the like; (b) a dosage form for non-oral administration, such as rectal, vaginal, urethral, intraocular, nasal or ear administration, including an aqueous suspension, an oily preparations and the like, or drops, a spray, suppositories, paste, ointments, etc.; (c) a dosage form for administration through for example subcutaneous, intraperitoneal, intravenous, intramuscular, intradermal, intraorbital, intracapsular, intramedullary and intrasternal injection; (d) a dosage form for local administration, including an inhalation solution, a nasal spray, an implant, and the like; and (e) another dosage form deemed suitable to deliver an active ingredient to a target tissue by those skilled in the art.

In some embodiments, the composition is in a dosage form selected from a tablet, a capsule, a powder and a suspension, and preferably a suspension.

Exact formula, route of administration and dosage of the composition can be selected by the physician according to the patient's condition. In some embodiments, the lamotrigine hydrate form A is administered to a patient at a dose of 0.1 mg/kg to 1000 mg/kg. Depending on the patient's need, the dose may be administered in one or more dose units in one day or over several days. In the case that a determined dose has been used in clinic, the composition of lamotrigine hydrate form A may be used at the determined dose, or at a range of about 0.1% to about 500% of the dose, more preferably of about 25% to about 250% of the dose.

A clinician may know how and when to terminate or adjust the dose based on toxicity or organ dysfunction. Conversely, in case of inadequate clinical reaction (toxic reaction excluded), a clinician may know how to adjust the therapeutic dose to a higher level. In the disease being treated, the amount of the dose may be adjusted according to the severity of the disease being treated and the route of administration. The severity of the disease may be assessed by, for example, standard prognostic assessment methods. In addition, the dose may also be adjusted according to age, weight and individual differences of patients.

Although the exact dose varies in various situations, in most cases, the dose may be summarized as follows: the daily dosage regimen for an adult patient may be from about 0.1 mg to about 2000 mg, preferably from about 1 mg to about 500 mg and most preferably from about 5 mg to about 200 mg for oral administration; and preferably from about 0.01 mg to about 100 mg and most preferably from about 0.1 mg to about 60 mg for intravenous, subcutaneous or intramuscular injection. In some embodiments, the composition is administered 1-4 times per day. In other cases, the lamotrigine hydrate form A may be administered by continuous intravenous infusion, preferably at a dose of at most about 1000 mg per day. A skilled person in the art may understand that in some cases, it may be necessary to use the lamotrigine hydrate form A at a dose in excess of or much higher than the above-mentioned preferred dose range, in order to effectively and actively treat a particularly critical condition. In some embodiments, the lamotrigine hydrate form A may be used continuously for one week or several months or several years or more.

In some embodiments, after administration of the composition comprising lamotrigine hydrate form A, it is released in about 1 hour to 12 hours, preferably 3 hours to 12 hours, more preferably 6 hours to 12 hours. In some embodiments, the orally administered composition of lamotrigine hydrate form A may be administered for 1-4 times per day in a single dose or multiple doses. The oral dosage form may be conveniently administered in a single dose and may be prepared by methods well known in the pharmaceutical field.

If desired, the composition comprising lamotrigine hydrate form A may be stored in a packaging material or a drug delivery device, which may include one or more unit doses. The packaging material may be a metal or plastic film, or a blister package. The package or drug delivery device may also be enclosed with instructions. Such instructions may be either prescription medicine labels approved by the drug administration, or instructions for formulating the composition comprising lamotrigine hydrate form A in a compatible container.

In some embodiments, in the composition containing lamotrigine hydrate form A, more than about 50%, more than about 60%, more than about 70%, more than about 80%, more than about 90% or more than about 95% of lamotrigine is present in the form of the lamotrigine hydrate form A. In some embodiments, in the composition, more than about 80% of lamotrigine is present in the form of the lamotrigine hydrate form A, preferably more than about 90% is present in the form of the lamotrigine hydrate form A in the composition, and more preferably, more than about 95% of lamotrigine is present in the form of the lamotrigine hydrate form A in the composition.

In some embodiments, a pharmaceutically acceptable excipient is selected from one or more of a thickener, a filler, a sweetener, a pH modifier, and a preservative.

In some embodiments, the thickener is selected from hydrocolloids, such as xanthan gum, guar gum, locust bean gum and carrageenan; cellulose derivatives, such as sodium carboxymethyl cellulose, hydroxypropyl cellulose, methyl cellulose and hydroxypropyl methyl cellulose; polysaccharides, such as starch and pregelatinized starch; alginates, such as sodium alginate; acrylic acid copolymers, such as carbomer; aluminum magnesium silicate; and a combination thereof.

In a preferred embodiment, the thickener is selected from one or more of xanthan gum, povidone, colloidal microcrystalline cellulose and sodium alginate, more preferably xanthan gum; and preferably, content of the thickener is about 1 to 7 parts by weight, preferably about 1 to 5 parts by weight, on the basis that content of the lamotrigine hydrate form A is about 10 parts by weight.

In a preferred embodiment, the filler is selected from one or more of mannitol, microcrystalline cellulose, sucrose and lactose; and preferably, content of the filler is about 20 to 60 parts by weight, on the basis that content of the lamotrigine hydrate form A is about 10 parts by weight.

In a preferred embodiment, the sweetener is selected from one or more of sucralose, aspartame and sodium saccharin; and preferably, content of the sweetener is about 1-3 parts by weight, on the basis that content of the lamotrigine hydrate form A is about 10 parts by weight.

In a preferred embodiment, the pH modifier is selected from one or more of sodium dihydrogen phosphate, citric acid and sodium citrate; and preferably, content of the pH modifier is about 2-5 parts by weight, on the basis that content of the lamotrigine hydrate form A is about 10 parts by weight.

In a preferred embodiment, the preservative is selected from one or more of sodium propyl hydroxybenzoate, sodium methyl hydroxybenzoate, sodium benzoate and potassium sorbate; and preferably, content of the preservative is about 1 to 3 parts by weight, on the basis that content of the lamotrigine hydrate form A is about 10 parts by weight.

In some embodiments, the composition comprises: about 10 parts by weight of the lamotrigine hydrate form A; about 1-5 parts by weight of xanthan gum; about 20-60 parts by weight of mannitol; about 1-3 parts by weight of sucralose; about 2-5 parts by weight of sodium dihydrogen phosphate; and about 1-3 parts by weight of a combination of sodium methyl hydroxybenzoate and sodium propyl hydroxybenzoate, where the weight ratio of sodium methyl hydroxybenzoate to sodium propyl hydroxybenzoate is about 9:1.

The composition comprising lamotrigine hydrate form A described above may be obtained by a certain formulation method with lamotrigine hydrate form A and other components. It may also be obtained by a certain formulation method with anhydrous lamotrigine, lamotrigine hydrate or lamotrigine salts and other components.

In another aspect, the invention provides a suspension comprising lamotrigine hydrate form A, a lamotrigine hydrate form A, a solid form comprising lamotrigine hydrate form A or a composition comprising lamotrigine hydrate form A, prepared by the method of the invention. As used herein, the term "solid form" includes all solid forms of lamotrigine, such as crystalline or amorphous forms, or a combination thereof.

In some embodiments, in the suspension comprising lamotrigine hydrate form A, the lamotrigine hydrate form A, the solid form comprising lamotrigine hydrate form A or the composition comprising lamotrigine hydrate form A, more than about 50%, more than about 60%, more than about 70%, more than about 80%, more than about 90% or more than about 95% of lamotrigine is present in the form of the lamotrigine hydrate form A.

Therapy Methods and Uses

In another aspect, the invention provides a method for treating a neurological disorder, comprising administering a therapeutically effective amount of the lamotrigine hydrate form A of the invention or the composition of the invention to a subject in need thereof.

In another aspect, the invention provides a use of the lamotrigine hydrate form A of the invention or the composition of the invention in preparation of a medicament for treating the neurological disorder.

In another aspect, the invention provides the lamotrigine hydrate form A of the invention or the composition of the invention for use in treating a neurological disorder.

In some embodiments, the lamotrigine hydrate form A may be used alone, or in combination with other medicaments for treating a neurological disorder.

In some embodiments, the lamotrigine hydrate form A has a purity of more than about 50%, more than about 60%, more than about 70%, more than about 80%, more than about 90%, or more than about 95%. In some embodiments, in the composition comprising lamotrigine hydrate form A, more than about 50%, more than about 60%, more than about 70%, more than about 80%, more than about 90% or more than about 95% of lamotrigine is present in the form of the lamotrigine hydrate form A, preferably more than about 90% of lamotrigine is present in the form of the lamotrigine hydrate form A, and more preferably, more than about 95% of lamotrigine is present in the form of the lamotrigine hydrate form A.

In some embodiments, the neurological disorder is selected from one or more of Alzheimer's disease, depression, multiple sclerosis, Parkinson's disease and epilepsy.

In some embodiments, the medicament is used in combination with another medicament for treating a neurological disorder, preferably, the another medicament is selected from one or more of oxcarbazepine, carbamazepine, topiramate and lacosamide.

In some embodiments, the medicament is in the form of suspension.

In some embodiments, in the medicament, more than about 80% of lamotrigine, preferably more than about 90%, and more preferably more than about 95% of lamotrigine, is present in the form of the lamotrigine hydrate form A.

The lamotrigine hydrate form A prepared by the invention is not only high in purity, but also has good solubility and high chemical stability, as well as a significant improved physical stability in an aqueous phase environment (i.e., the suspension prepared by the invention has a better physical stability). As such, it is suitable for controlling of long-term epilepsy.

The following examples are only used to further illustrate the present invention, but the scope of the present invention is not limited to these examples. The raw materials and reagents used herein may be commercially available.

Example 1: Preparation of a Suspension Comprising Lamotrigine Hydrate Form A Using Lamotrigine Particles Having Different Particle Sizes 10 parts by weight of lamotrigine particles (D90) having a particle size of 8 μm, 12 μm and 60 μm respectively (available from Aurobindo Pharma Co., Ltd., India), and 3 parts by weight of xanthan gum (available from CP Kelco, USA), were added to 1000 parts by weight of purified water. It was dispersed uniformly, and then allowed to stand at 4° C. for 24 hours to obtain the suspension. The resulting suspension was left at room temperature for 1 month, and the suspension and the crystal forms therein were checked at different time points. The results are shown in Table 1:

Unless stated otherwise, the XRPD results in the examples were measured by a Bruker D8 advance x-ray diffraction instrument (Germany), and the microscope results were measured on a Nanpai CM2000S microscope (Nanjing, China).

TABLE 1

| Standing conditions for different formulas | | Check item | | |
|---|---|---|---|---|
| | | Appearance | Particle size on microscope | Crystal form by XRPD |
| Lamotrigine particles having a particle size of 8 μm | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| Lamotrigine particles having a particle size of 12 μm | At room temperature at zero point | Milky white suspension | 20-30 μm | Lamotrigine hydrate form A |
| | At room temperature for 1 week | Milky white suspension | 60-70 μm | Lamotrigine hydrate form A |
| | At room temperature for 1 month | Milky white suspension | 60-70 μm | Lamotrigine hydrate form A |
| Lamotrigine particles having a particle size of 60 μm | At room temperature at zero point | Milky white suspension | 50-70 μm | Lamotrigine hydrate form A containing unknown crystals |
| | At room temperature for 1 week | Milky white suspension | 50-70 μm | Lamotrigine hydrate form A containing unknown crystals |
| | At room temperature for 1 month | Milky white suspension | 50-70 μm | Lamotrigine hydrate form A containing unknown crystals |

Figure 3:
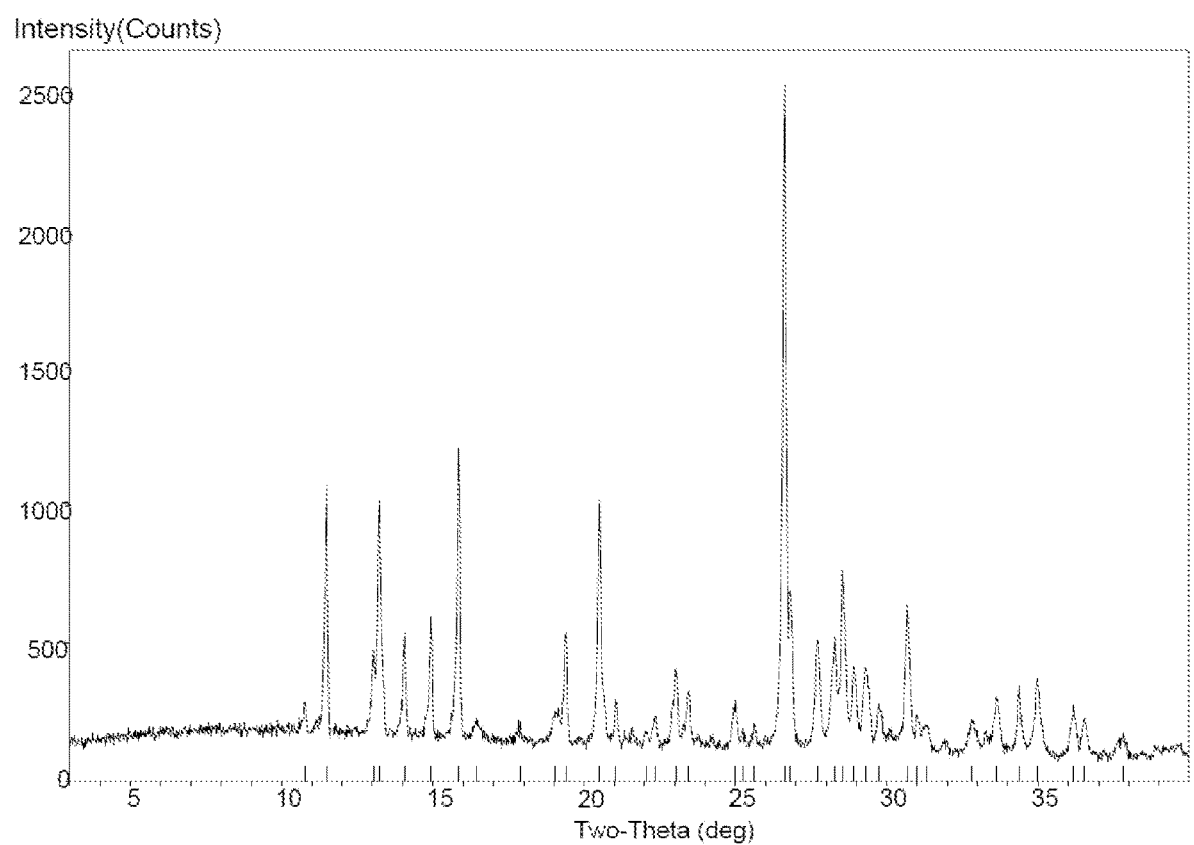
FIG. 3 shows an XRPD spectrum of a lamotrigine hydrate form A comprising unknown crystals.

As shown in Table 1, the crystal form in the suspension is the lamotrigine hydrate form A when using the lamotrigine particles having a particle size of 8 μm and 12 μm, respectively. When using the lamotrigine particles having a particle size of 60 μm, unknown crystals were included in the crystal form in the suspension, which makes it impossible to ensure the stability of crystal properties. The XRPD results of the lamotrigine hydrate form A containing unknown crystals are shown in FIG. 3.

Example 2: Preparation of a Suspension Comprising Lamotrigine Hydrate Form A Using Different Thickeners 10 parts by weight of lamotrigine particles having a particle size (D90) of 8 μm and 3 parts by weight of a thickener (xanthan gum (available from CP Kelco, USA), povidone (available from BASF, Germany), colloidal microcrystalline cellulose (available from FMC, USA) and sodium alginate (available from Qingdao Bright Moon Seaweed Group Co., Ltd.)) were added to 1000 parts by weight of purified water. It was dispersed uniformly, and then allowed to stand at 4° C. for 24 hours to obtain the suspension. The resulting suspension was left at room temperature for 1 month, and the suspension and the crystal forms therein were checked at different time points. The results are shown in Table 2:

TABLE 2

| Standing conditions for different formulas | | Chem item | | |
|---|---|---|---|---|
| | | Appearance | Particle size on microscope | Crystal form by XRPD |
| xanthan gum as a thickener | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| Povidone as a thickener | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |

TABLE 2-continued

| Standing conditions for different formulas | | Appearance | Particle size on microscope | Crystal form by XRPD |
|---|---|---|---|---|
| Colloidal microcrystalline cellulose as a thickener | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| Sodium alginate as a thickener | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |

As shown in Table 2, when xanthan gum, povidone, colloidal microcrystalline cellulose and sodium alginate were used as the thickener respectively, the crystal form in each resulting suspension was the lamotrigine hydrate form A.

Example 3: Preparation of a Suspension Comprising Lamotrigine Hydrate Form A with Different Amounts of a Thickener Content 10 parts by weight of lamotrigine particles having a particle size (D90) of 8 μm together with xanthan gum of 0 parts by weight, 1 part by weight and 5 parts by weight respectively were added to 1000 parts by weight of purified water. It was dispersed uniformly and, then allowed to stand at 4° C. for 24 hours to obtain the suspension. The resulting suspension was left at room temperature for 1 month, and the suspension and the crystal forms therein were checked at different time points. The results are shown in Table 3:

TABLE 3

| Standing conditions for different formulas | | Appearance | Particle size on microscope | Crystal form by XRPD |
|---|---|---|---|---|
| 0 parts by weight of xanthan gum | At room temperature at zero point | Milky white suspension | 20-30 μm | Lamotrigine hydrate form A |
| | At room temperature for 1 week | Milky white suspension | 20-30 μm | Lamotrigine hydrate form A containing unknown crystals |
| | At room temperature for 1 month | Milky white suspension | 20-30 μm | Lamotrigine hydrate form A unknown crystals |
| 1 part by weight of xanthan gum | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| 5 parts by weight of xanthan gum | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |

As shown in Table 3, the crystal form in the suspension is lamotrigine hydrate form A when using the thickeners of 1 part by weight and 5 parts by weight respectively. Without using the thickener, the crystal form in the suspension after one week at room temperature contains unknown crystals, which makes impossible to ensure the stability of crystal properties.

Example 4: Preparation of a Suspension Comprising Lamotrigine Hydrate Form A when Standing at Different Low Temperatures 10 parts by weight of lamotrigine particles having a particle size (D90) of 8 μm and 3 parts by weight of xanthan gum were added to 1000 parts by weight of purified water. It was dispersed uniformly, and then allowed to stand at low temperature (−20° C., 4° C. and 20° C., respectively) for 24 hours to obtain the suspension. The resulting suspension was left at room temperature for 1 month, and the suspension and the crystal forms therein were checked at different time points. The results are shown in Table 4:

TABLE 4

| Standing conditions for different formulas | | Appearance | Particle size on microscope | Crystal form by XRPD |
|---|---|---|---|---|
| Standing at −20° C. | At room temperature at zero point | NA | NA | NA |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| Standing at 4° C. | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |
| Standing at 20° C. | At room temperature at zero point | Milky white suspension | 20-30 μm | Lamotrigine hydrate form A |
| | At room temperature for 1 week | Milky white suspension | 20-30 μm | Lamotrigine hydrate form A |
| | At room temperature for 1 month | Milky white suspension | 20-30 μm | Lamotrigine hydrate form A |

As shown in Table 4, the crystal form in the suspension was lamotrigine hydrate form A when standing at a low temperature of −20° C., 4° C. and 20° C., respectively.

Example 5: Preparation of a Suspension Comprising Lamotrigine Hydrate Form A by Standing at a Low Temperature for Different Periods 10 parts by weight of lamotrigine particles having a particle size (D90) of 8 μm and 3 parts by weight of xanthan gum were added to 1000 parts by weight of purified water. It was dispersed uniformly, and then allowed to stand at 4° C. for 0 hours, 2 hours, 8 hours and 24 hours respectively, to obtain the suspension. The resulting suspension was left at room temperature for 1 month, and the suspension and crystal forms therein were checked at different times. The results are shown in Table 5:

TABLE 5

| Standing conditions for different formulas | | Appearance | Particle size on microscope | Crystal form by XRPD |
|---|---|---|---|---|
| Standing at 4° C. for 0 hour | At room temperature at zero point | Milky white suspension | 20-30 μm | Anhydrous |
| | At room temperature for 1 week | Milky white suspension | 20-30 μm | Lamotrigine hydrate form A containing unknown crystals |
| | At room temperature for 1 month | Milky white suspension | 20-30 μm | Lamotrigine hydrate form A containing unknown crystals |
| Standing at 4° C. for | At room temperature at zero point | Milky white suspension | 20-30 μm | Lamotrigine hydrate form A |

TABLE 5-continued

| Standing conditions for different formulas | | Appearance | Particle size on microscope | Crystal form by XRPD |
|---|---|---|---|---|
| 2 hours | At room temperature for 1 week | Milky white suspension | 20-30 μm | Lamotrigine hydrate form A |
|  | At room temperature for 1 month | Milky white suspension | 20-30 μm | Lamotrigine hydrate form A |
| Standing at 4° C. for 8 hours | At room temperature at zero point | Milky white suspension | 20-30 μm | Lamotrigine hydrate form A |
|  | At room temperature for 1 week | Milky white suspension | 20-30 μm | Lamotrigine hydrate form A |
|  | At room temperature for 1 month | Milky white suspension | 20-30 μm | Lamotrigine hydrate form A |
| Standing at 4° C. for 24 hours | At room temperature at zero point | Milky white suspension | 20-30 μm | Lamotrigine hydrate form A |
|  | At room temperature for 1 week | Milky white suspension | 20-30 μm | Lamotrigine hydrate form A |
|  | At room temperature for 1 month | Milky white suspension | 20-30 μm | Lamotrigine hydrate form A |

As shown in Table 5, the crystal form in the suspension was lamotrigine hydrate form A when standing at a low temperature for 2 hours, 8 hours and 24 hours, respectively. Without standing at a low temperature (i e standing at 4° C. for 0 hours), after being left at room temperature for one week, the crystal form in the suspension contained unknown crystals, which makes impossible to ensure the stability of crystal properties.

Example 6: Dissolution and Stability 2.5 ml of the resulting suspension prepared by standing at 4° C. for 24 hours described in Example 5 was taken, and dissolution of the lamotrigine hydrate form A in the suspension was determined by paddling at a rotating speed of 50 rpm and a temperature of 37±0.5° C., with a dissolution medium of 900 ml 0.1 N hydrochloric acid. The dissolution exceeded 85% (w/w) at 15 min. This dissolution result was consistent with that of the marketed immediate-release lamotrigine tablets (Lamictal® 25 mg), showing that the dissolution of the lamotrigine hydrate form A can meet clinical application.

The prepared suspension was left at room temperature for 1 month, and the suspension and crystal forms therein were checked at different times, with the following check items: appearance, particle size on microscope, crystal form by XRPD, dissolution, content and related materials. The results are shown in Table 6. The results obtained at different time all met limit requirements, showing that the suspension has good stability and can meet the need for long-term medication of a patient.

Determination of dissolution: paddling was applied at a rotating speed of 50 rpm and a temperature of 37±0.5° C., with a dissolution medium of 900 ml 0.1 N hydrochloric acid. Sampling was taken at 15 min, and the dissolution was determined by ultraviolet spectrophotometry.

Determination of content and related materials: a certain amount of suspension was taken, and after reaching a metered volume with a mobile phase and methanol, HPLC was applied for such determination

TABLE 6

| | Check item | | | | | |
|---|---|---|---|---|---|---|
| Standing conditions | Appearance | Particle size on microscope | Crystal form by XRPD | Dissolution | Content | Related materials |
| Limit requirements | Milky white suspension | No more than 80 μm | Hydrate form A | Dissolution exceeded 85% at 15 min | 90%-110% of the labelled amount | Impurity C: no more than 0.2%; unknown individual impurities: no more than 0.2%; total impurities: no more than 1.0% |
| At room temperature at zero point | Milky white suspension | 20-30 μm | Hydrate form A | 95.4% (15 min) | 100.4% | Impurity C: undetected; unknown individual impurities: undetected; total impurities: undetected |
| At room temperature for 1 month | Milky white suspension | 20-30 μm | Hydrate form A | 97.5% (15 min) | 101.1% | Impurity C: undetected; unknown individual impurities: undetected; total impurities: undetected |

Example 7

10 parts by weight of lamotrigine particles having a particle size (D90) of 12 μm and 7 parts by weight of xanthan gum were added to 1000 parts by weight of purified water. It was dispersed uniformly, and then allowed to stay at 4° C. for 24 hours to obtain a suspension comprising lamotrigine hydrate form A. The suspension was filtered to obtain the lamotrigine hydrate form A.

The obtained lamotrigine hydrate form A was analyzed by XRPD. The XRPD spectrum of the lamotrigine hydrate form A has a series of characteristic peaks at diffraction angles (2θ) of 11.5±0.2°, 13.4±0.2°, 15.0±0.2°, 16.5±0.2°, 19.2±0.2°, 26.9±0.2° and 27.7±0.2° and no characteristic peak at a diffraction angle (2θ) of 15.9±0.2°.

The obtained lamotrigine hydrate form A was quantitatively analyzed by XRPD. Al$_2$O$_3$ was selected as the standard material, and the XRPD was performed using a Braker D8 advance instrument under voltage of 40 kV, current of 40 mA, step of 0.02 degrees, and a scanning speed of 0.1 seconds/step. The purity of the lamotrigine hydrate form A was measured as 87.2% (w/w).

Example 8

10 parts by weight of lamotrigine particles having a particle size (D90) of 8 μm and 3 parts by weight of povidone were added to 1000 parts by weight of purified water. It was dispersed uniformly, and then allowed to stand at 20° C. for 2 hours to obtain a suspension comprising lamotrigine hydrate form A. The suspension was filtered to obtain the lamotrigine hydrate form A.

The obtained lamotrigine hydrate form A was analyzed by XRPD. The XRPD spectrum of the lamotrigine hydrate form A has a series of characteristic peaks at diffraction angles (2θ) of 11.5±0.2°, 13.4±0.2°, 15.0±0.2°, 16.5±0.2°, 19.2±0.2°, 26.9±0.2° and 27.7±0.2°, and no characteristic peak at diffraction angles (2θ) of 23.5±0.2°, 28.2±0.2° and 30.7±0.2°.

The lamotrigine hydrate form A showed an appearance of short prism on microscope.

The obtained lamotrigine hydrate form A was quantitatively analyzed by XRPD. Al$_2$O$_3$ was selected as the reference material, and XRPD was performed using a Braker D8 advance instrument under voltage of 40 kV, current of 40 mA, step of 0.02 degrees, and a scanning speed of 0.1 seconds/step. The purity of lamotrigine hydrate form A was measured as 91.4% (w/w).

Example 9

10 parts by weight of lamotrigine particles having a particle size (D90) of 8 μm and 3 parts by weight of xanthan gum were added to 1000 parts by weight of purified water. It was dispersed uniformly, and then allowed to stand at 4° C. for 24 hours to obtain a suspension comprising lamotrigine hydrate form A. The suspension was filtered to obtain the lamotrigine hydrate form A.

The obtained lamotrigine hydrate form A was analyzed by XRPD. The XRPD spectrum of the lamotrigine hydrate form A has a series of characteristic peaks at diffraction angles (2θ) of 11.5±0.2°, 13.4±0.2°, 15.0±0.2°, 16.5±0.2°, 19.2±0.2°, 26.9±0.2° and 27.7±0.2°, and no characteristic peak at diffraction angles (2θ) of 15.9±0.2°, 20.5±0.2°, 23.5±0.2°, 28.2±0.2° and 30.7±0.2°.

The obtained lamotrigine hydrate form A was quantitatively analyzed by XRPD. Al2O3 was selected as the reference material, and XRPD was performed using a Bruker D8 advance instrument under voltage 40 kV, current of 40 mV, step of 0.02 degrees, and a scanning speed: of 0.1 seconds/step. The purity of lamotrigine hydrate form A was measured as 97.7% (w/w). It has an XRPD spectrum shown in FIG. 1, and an appearance on microscope shown in FIG. 2.

Example 10 Suspension 10 parts by weight of lamotrigine particles having a particle size (D90) of 8 μm, 5 parts by weight of xanthan gum, 20 parts by weight of mannitol (available from Roquette, France), 1 part by weight of sucralose (available from Merck, Germany) and 2 parts by weight of sodium dihydrogen phosphate (available from Spectrum Chemical Mfg. Corp., USA) and 1 part by weight of sodium methyl hydroxybenzoate (available from Spectrum Chemical Mfg. Corp., USA) were added to 5000 parts by weight of purified water. It was dispersed uniformly, and then allowed to stand at 20° C. for 30 minutes, resulting in a suspension comprising lamotrigine hydrate form A. The resulting suspension is a suspension comprising the lamotrigine hydrate form A that is ready to be administered to a patient.

Example 11 Dry Suspension 10 parts by weight of lamotrigine particles having a particle size (D90) of 30 μm, 3 parts by weight of xanthan gum, 20 parts by weight of mannitol, 1 part by weight of sucralose, 2 parts by weight of sodium dihydrogen phosphate and 2 parts by weight of a combination of sodium methyl hydroxybenzoate and sodium propyl hydroxybenzoate (the weight ratio of sodium methyl hydroxybenzoate to sodium propyl hydroxybenzoate was 9:1) were screened through a 1016 micron screen mesh respectively, and then were all placed in a hopper having a suitable size and mixed at 20 rpm for 10 minutes. A dry suspension was obtained for further application.

The above-mentioned dry suspension was added to purified water for reconstitution before administration to a patient. Particularly, the dry suspension was added to purified water, and the mixture was uniformly dispersed by shaking manually, then allowed to stand at 4° C. for 24 hours to obtain the suspension containing lamotrigine hydrate form A ready to applied to a patient.

Example 12

All components of the prescription shown in Table 7 were screened through a 1016 micron screen mesh respectively, and then were all placed in a hopper having a suitable size and mixed at 20 rpm for 10 minutes. A dry suspension was obtained for further application. The above-mentioned dry suspension was added to purified water for reconstitution before administration to a patient. Particularly, the dry suspension was added to the purified water, and the mixture was uniformly dispersed by shaking manually, then allowed to stand at 4° C. for 24 hours to obtain the suspension containing lamotrigine hydrate form A ready to be applied to a patient.

More than 95% of lamotrigine in the suspension is present in the form of lamotrigine hydrate form A.

TABLE 7

| Component | Dosage, g/bottle | Function |
|---|---|---|
| Lamotrigine particles (D90 = 8 μm) | 1 | Active ingredient |
| Sucrose | 2 | Filler |
| Xanthan gum | 0.3 | Thickener |
| Sodium dihydrogen phosphate | 0.3 | pH modifier |
| Sucralose | 0.1 | Sweetener |
| Sodium methyl hydroxybenzoate | 0.18 | Preservative |
| Sodium propyl hydroxybenzoate | 0.02 | Preservative |

Example 13 Tablet 10 parts by weight of lamotrigine hydrate form A and 30 parts by weight of microcrystalline cellulose were screened through a 1016 micron screen mesh respectively, and then were all placed in a hopper having a suitable size and mixed at 20 rpm for 10 minutes. The mixture was placed in a tablet press to be pressed at 20 rpm and a hardness of 80N, resulting in a tablet containing lamotrigine hydrate form A ready to be administered to a patient. The specification of the tablet is 100 mg. The tablet may be used for treating a neurological disorder.

Example 14 Capsule 10 parts by weight of lamotrigine hydrate form A, 10 parts by weight of oxcarbazepine, 3 parts by weight of xanthan gum and 30 parts by weight of lactose were screened through a 1016 micron screen mesh respectively. They were then all placed in a hopper having a suitable size and mixed at 20 rpm for 10 minutes. The mixture was placed in a wet granulator, and water was added to prepare wet particles at a shearing speed of 200 rpm and a stirring speed of 200 rpm. After the granulating, the wet particles were dried over a fluidized bed at 40° C. to obtain dry particles, which then were screened through a 1016 micron screen mesh to obtain particles of a formulation. After filling the particles into 1# capsule by a capsule filling machine, a capsule containing lamotrigine hydrate form A ready to be administered to a patient was obtained. The capsule can be used for treating epilepsy.

The above-mentioned examples only intend to describe several embodiments of the present invention, which were described specifically in details, but should not be understood as limitation to the scope of the invention. It is appreciated by those skilled in the art that several variations and modifications may also be possible without departing from the concept of the present invention. Such variations and modifications fall within the patentable scope of the present invention. As such, the scope of the present invention is subject to the appended claims

The invention claimed is:

1. A method for preparing lamotrigine hydrate form A in a suspension, comprising the steps of:
adding lamotrigine particles and a thickener to an aqueous phase;
dispersing the lamotrigine particles having a particle size (D90) ranging from about 8 to about 12 μm and the thickener uniformly in the aqueous phase; and cooling the aqueous phase at a temperature lower than 25° C. to obtain the suspension comprising the lamotrigine hydrate form A, wherein the form A has a particle size ranging from about 20 to about 30 μm in the suspension, wherein the term about indicates a range within ±1 of a given value,
wherein an XRPD spectrum of the lamotrigine hydrate form A comprises characteristic peaks at diffraction angles (2θ) of about 11.5±0.2°, 13.4±0.2°, 15.0±0.2°, 16.5±0.2°, 19.2±0.2°, 26.9±0.2° and 27.7±0.2°, and has no characteristic peaks at one or more diffraction angles (2θ) of 15.9±0.2°, 20.5±0.2°, 23.5±0.2°, 28.2±0.2° and 30.7±0.2°,
wherein the thickener comprises xanthan gum, povidone, colloidal microcrystalline cellulose, or sodium alginate,
wherein more than 90% of lamotrigine in the suspension is present in the form of the lamotrigine hydrate form A.

2. The method according to claim 1, wherein the lamotrigine particles have a particle size (D90) of about 8 μm.

3. The method according to claim 1, wherein the thickener is xanthan gum.

4. The method according to claim 1, wherein the aqueous phase optionally comprises a pH modifier and a sweetener; and the aqueous phase is 100 to 5000 parts by weight to 10 parts by weight of the lamotrigine particles.

5. The method according to claim 1, wherein the temperature for cooling the aqueous phase is lower than 20° C.

6. The method according to claim 5, wherein the aqueous phase is cooled for at least 30 minutes.

7. The method according to claim 1, wherein the time interval between the dispersing uniformly and the cooling at standing is up to 12 hours.

8. The method according to claim 1, wherein the lamotrigine particles and the thickener and one or more of a filler, a sweetener, a pH modifier and a preservative are admixed before being added to the aqueous phase.

9. The method according to claim 8, wherein the filler is one or more of mannitol, microcrystalline cellulose, sucrose and lactose, and the filler is 20-60 parts by weight to 10 parts by weight of the lamotrigine particles; the sweetener is one or more of sucralose, aspartame and sodium saccharin, and the sweetener is 1-3 parts by weight to 10 parts by weight of the lamotrigine particles; the pH modifier is one or more of sodium dihydrogen phosphate, citric acid, and sodium citrate, and the pH modifier is 2-5 parts by weight to 10 parts by weight of the lamotrigine particles; and the preservative is one or more of sodium propyl hydroxybenzoate, sodium methyl hydroxybenzoate, sodium benzoate and potassium sorbate, and the preservative is 1-3 parts by weight to 10 parts by weight of the lamotrigine particles.

10. The method according to claim 1, wherein more than 95% lamotrigine is present in the form of the lamotrigine hydrate form A.

11. A pharmaceutical composition comprising the lamotrigine hydrate form A in the suspension prepared according to claim 1 and one or more pharmaceutically acceptable excipients.

12. The method according to claim 1, where the size of the lamotrigine particles is selected so that the form A maintains a particle size ranging from about 20 to about 30 μm in the suspension for at least 1 week.

13. The method according to claim 1, where the size of the lamotrigine particles is selected so that the form A maintains a particle size ranging from about 20 to about 30 μm in the suspension for about 1 month.

14. The method according to claim 1, where the aqueous phase is substantially water.

15. The method according to claim 1, further comprising adding to the aqueous phase a preservative selected from the group consisting of sodium propyl hydroxybenzoate, sodium methyl hydroxybenzoate, sodium benzoate and potassium sorbate.

16. The method according to claim 1, wherein the pH modifier comprises one or more of sodium dihydrogen phosphate, citric acid, and sodium citrate.

17. The method according to claim 1, wherein the XRPD spectrum of the lamotrigine hydrate form A comprises the characteristic peaks at substantially same diffraction angles (2θ) as shown in FIG. 1.

18. The method according to claim 1, wherein the aqueous phase is allowed to stand without stirring to form the lamotrigine hydrate form A in the suspension.

19. The method according to claim 1, wherein the temperature is equal or lower than 20° C.

\* \* \* \* \*